(12) United States Patent
Datwyler et al.

(10) Patent No.: US 8,658,384 B2
(45) Date of Patent: Feb. 25, 2014

(54) BIOMARKERS FOR PREDICTION OF MAJOR ADVERSE CARDIAC EVENTS AND USES THEREOF

(71) Applicant: Abbott Laboratories, Abbott Park, IL (US)

(72) Inventors: Saul A. Datwyler, Evanston, IL (US); Jessie W. Shih, Lake Forest, IL (US); Robert C. Doss, Liberyville, IL (US); Walter J. Keirans, Libertyville, IL (US); Sudarshan Hebbar, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/926,647

(22) Filed: Jun. 25, 2013

(65) Prior Publication Data

US 2013/0288269 A1    Oct. 31, 2013

Related U.S. Application Data

(62) Division of application No. 12/871,056, filed on Aug. 30, 2010, now Pat. No. 8,501,420.

(60) Provisional application No. 61/238,547, filed on Aug. 31, 2009.

(51) Int. Cl.
*G01N 31/00* (2006.01)
*G01N 33/53* (2006.01)

(52) U.S. Cl.
USPC ........ 435/7.21; 435/7.1; 435/287.9; 436/501; 436/518; 427/287; 427/337; 427/338; 530/300; 530/350

(58) Field of Classification Search
None
See application file for complete search history.

(56) References Cited

U.S. PATENT DOCUMENTS 8,501,420 B2 *   8/2013   Datwyler et al. ............ 435/7.21

* cited by examiner

*Primary Examiner* — Lisa Cook
(74) *Attorney, Agent, or Firm* — Cheryl L. Becker

(57) ABSTRACT

The present invention relates to combinations of biomarkers and levels thereof that may be used, for example, in the determination of risk associated with the occurrence of a major adverse cardiac event (MACE) in a patient.

9 Claims, 4 Drawing Sheets

BIOMARKERS FOR PREDICTION OF MAJOR ADVERSE CARDIAC EVENTS AND USES THEREOF

The subject application is a divisional of allowed U.S. patent application Ser. No. 12/871,056, filed on Aug. 30, 2010, now U.S. Pat. No. 8,501,420 which claims priority to abandoned U.S. Provisional Patent Application Ser. No. 61/238,547, filed on Aug. 31, 2009, both herein incorporated in their entirety by reference.

BACKGROUND OF THE INVENTION

1. Field of the Invention

The present invention relates to combinations of biomarkers that may be used, for example, in the prognosis or determination of future risk associated with the occurrence of a major adverse cardiac event (MACE) in a patient over a particular period of time.

2. Background Information

The ability to predict the risk of future major adverse cardiac events in patients presenting with signs and symptoms of acute coronary syndrome (ACS) is a significant achievement. Major adverse cardiac event (MACE) typically refers to the endpoints of death (either all cause or cardiac related), myocardial infarction (MI) and revascularization (either percutaneous coronary revascularization or coronary artery bypass surgery). Secondary endpoints often include congestive/chronic heart failure (CHF), stroke, re-revascularization and hospitalization for ACS or life threatening dysrythmias. In particular, with early determination of risk level, patients having a significant risk of such events can lower this risk by obtaining appropriate therapeutic intervention whether through surgery, administration of medications, changes in diet and exercise and/or periodic cardiac monitoring.

Acute coronary syndrome covers a group of clinical symptoms compatible with acute myocardial ischemia which is chest pain due to insufficient blood supply to the heart. In particular, it covers a spectrum of clinical conditions ranging from unstable angina to non-ST elevation myocardial infarction and ST-elevation myocardial infarction. The Redefinition of myocardial infarction in 2000 (J Am Coll Cardiol. 2000; 36:959-969) and the new Universal Definition of myocardial infarction in 2007 (Thygesen et al., J Am Coll Cardiol. 2007; 50:2173-95) established troponin as the definitive biomarker for the diagnosis of myocardial infarction along with clinical symptoms. Troponin was identified as the preferred marker, replacing CK-MB. Troponin I and T were first identified as serum markers of myocardial injury in the late 1970's (Clin. Sci. 1979; 56:30) and assays were described in the late 1980's (Am Heart J. 1987; 113:1333-44 and J. Mol. Cell. Cardiol. 1989; 21:1349-1353).

Troponin is a complex of three troponin molecules (i.e., Troponin I, Troponin T and Troponin C). Troponin T binds the troponin complex to tropomyosin, troponin I modulates the interaction of actin and myosin as an inhibitor of the actomyosin adenosine triphosphatase activity and troponin C is the calcium binding unit. The troponin complex is found in all striated muscle tissue including both skeletal and cardiac muscle. Troponin C exists in only one form in all types of striated muscle; on the other hand, troponin I and troponin T are found in three isoforms specific for cardiac, fast and slow muscle. The cardiac specific forms of Troponin I and Troponin T are the forms used for diagnosis of myocardial infarction. (The cardiac forms are denoted by a lower case c before the name, i.e., cTnI and cTnT.) cTnI and cTnT are released from the heart upon cardiac cell necrosis. Small cytosolic pools of Tn are known to exist and are released prior to further breakdown of muscle cells. The original literature describes the release of troponin as starting some 4-6 hours post injury (Wu et al., Clin Chem. 1999; 45:1104-21) and peaking at 12-16 hours; however, with newer, more sensitive assays, it appears that troponin is released much earlier, perhaps as soon as myoglobin.

The troponins circulate in the blood in several different forms. The exact circulating forms are not fully characterized, but it appears that the majority of the circulating cTnI is in a binary complex with TnC (Katrukha et al., Clin Chem. 1997; 43:1379-85), followed by the ternary complex of cTnI-TnC-cTnT, with very little free cTnI circulating. In addition, cTnI can be phosphorylated, reduced/oxidized and bound to heparin.

Previous studies have demonstrated the utility of single markers to risk stratify patients near term (i.e., 30 to 42 days) or mid term (i.e., 6 months) post initial presentation to the hospital. Ohman et al. and Antman et al. (NEJM 1996; 325: 1331-41 and 1342-9) demonstrated the utility of troponin for near-term risk stratification. A substudy of the Global Use of Strategies to Open Occluded Coronary Arteries in Acute Coronary Syndromes (GUSTO-IIa) investigated the potential of cardiac Troponin T (cTnT) to risk stratify patients with acute myocardial ischemia. Mortality within 30 days was significantly higher in patients with elevated cTnT levels. In the TIMI (Thrombolysis in Myocardial Infarction) IIIB trial, samples from patients with Acute Coronary Syndrome were analyzed for cardiac Troponin I (cTnI) and the relation between the level of cTnI and mortality at 42 days was determined There was a statistically significant increase in mortality with increasing levels of cTnI.

In another study, the ability of B-Type Natriuretic peptide (BNP) to predict risk in patients with unstable angina and non-ST-elevation myocardial infarction was evaluated (Morrow et al., J Am Coll Cardiol. 2003; 41:1264-72). Samples from patients enrolled in the TACTICS-TIMI (Treat Angina with Aggrastat and determine Cost of Therapy with an Invasive or Conservative Strategy. Thrombolysis in Myocardial Infarction) 18 trial were evaluated. The ability to use BNP for risk assessment and clinical decision making over a range of cut points, alone and with cTnI in patients with non-ST-elevation acute coronary syndrome (ACS), was evaluated. Events were evaluated at seven days and six months. Patients with elevated BNP (>80 pg/mL) were at higher risk of death at seven days and 6 months, and this association was independent of cTnI. Patients with elevated BNP were also at higher risk for development of congestive heart failure (CHF) at 30 days. The authors concluded that elevated BNP at presentation identified patients with non-ST-elevation ACS who were at higher risk of death and CHF and adds incremental information to cTnI.

In addition to single markers, panels of biomarkers have been evaluated for their ability to risk stratify patients with acute coronary syndrome. Individual markers, as mentioned above, have been shown to predict adverse cardiac events. The utility of markers in combination to predict adverse cardiac events was evaluated using sample from patients enrolled in the OPUS-TIMI (Orbofiban in Patients with Unstable coronary Syndromes-Thrombolysis in Myocardial Infarction) study (Sabatine et al., Circulation. 2002; 105: 1760-3). Baseline measurements of cTnI, CRP (c-Reactive protein) and BNP were measured. Elevations in cTnI, CRP and BNP each were independent predictors of death, myocardial infarction, or congestive heart failure. Categorizing the patients on the basis of number of elevated markers was associated with a near doubling of mortality risk for each additional positive marker. Similar relationships were also shown for the endpoints of MI, CHF and the composite at both 30 days and through 10 months.

A similar study utilizing the samples from patients in TACTICS-TIMI investigated a different panel of markers (Morrow et al. Eur. Heart J. 2008; 29:1096-1102). The prognostic utility of myeloperoxidase (MPO), soluble CD40 ligand (sCD40L), BNP, high sensitivity CRP (hsCRP) and cTnI for non-fatal recurrent ischemic events in non-ST-elevation ACS was investigated. Elevated baseline MPO was indicative of higher risk of non-fatal myocardial infarction or rehospitalization for ACS at 30 days. Stratification using baseline MPO, BNP and cTnI identified a >3-fold risk at 30 days for recurrent ischemic events. sCD40L was not associated with increased risk in this population.

In view of the above, there is a tremendous need for a significant and accurate predictor of major adverse cardiac events such that intervention can occur prior to the event of cardiac damage, damage that may be irreversible or even fatal. More specifically, biomarkers and the use thereof, as described herein, offer the ability to predict such events and thus allow physicians and patients the opportunity to implement the appropriate steps in order to save lives which would otherwise be lost without such prognostic information.

All patents and publications referred to herein are hereby incorporated in their entirety by reference.

SUMMARY OF THE INVENTION

The present invention encompasses a method of determining risk of experiencing a major adverse cardiac event (MACE), in a patient, within one year from presentation of at least one symptom of acute coronary syndrome (ACS). This method comprises the steps of: a) obtaining a test sample from the patient; b) determining the amount of at least three biomarkers selected from the group consisting of Troponin I (TnI), pro-B-type natriuretic peptide (proBNP) or a cleavage product thereof, high sensitivity C reactive protein (hsCRP), myeloperoxidase (MPO), placental growth factor (PlGF), estimated glomerular filtration rate (eGFR), homocysteine (HCY), choline, ischemia modified albumin (IMA), soluble CD40 ligand (sCD40L) and lipoprotein-associated phospholipase A2 (LpPLA2) in the test sample; and c) comparing the amount of the at least three biomarkers to biomarker reference standards, wherein the risk is determined by results of the comparison. In particular, these at least three biomarkers may be selected from the group consisting of, for example, proBNP or a cleavage product thereof, PlGF, eGRF and homocysteine. Alternatively, the at least three biomarkers are selected from the group consisting of, for example, proBNP or a cleavage product thereof (e.g., BNP or NT-proBNP), PlGF and eGFR. Additionally, the at least three biomarkers are selected from the group consisting of, for example, cTnI, proBNP or a cleavage product thereof and PlGF. Alternatively, the at least three biomarkers are selected from, for example, the group consisting of cTnI, proBNP or a cleavage product thereof, choline and eGFR. The test sample may be selected from the group consisting of blood, serum, and plasma. The results may be used to determine risk of experiencing a major adverse cardiac event within one year of presentation of at least one symptom of acute coronary symptom subsequent to stress testing undergone by the patient. The major adverse cardiac event comprises at least one condition selected from the group consisting of, for example, a myocardial infarction, death and revascularization, repeat revascularization, stroke, heart failure and dysrhymias. Additionally, the present invention includes a method of determining risk of experiencing a major adverse cardiac event, in a patient, within one year from presentation of at least one symptom of ACS comprising the step of: assessing the level of BNP in a test sample from the patient, wherein a BNP level less than or equal to approximately 150 pg/mL indicates that the level of PlGF in said test sample must be assessed and a BNP level greater than approximately 150 pg/mL indicates that the eGRF of the patient must be assessed, wherein if the PlGF level must be assessed, a PlGF level less than or equal to approximately 19.5 pg/mL indicates that the level of BNP in the test sample must be reassessed, wherein if the level of BNP must be reassessed, a BNP level less than or equal to approximately 65 pg/mL indicates the patient has a low risk of experiencing a major adverse cardiac event within one year from presentation of at least one symptom of ACS and a BNP level greater than approximately 65 pg/mL indicates the patient has a moderate risk of experiencing a major adverse cardiac event within one year from presentation of at least one symptom of ACS, and wherein if eGFR must be assessed, an eGFR level greater than approximately 68 mL/min/1.73 $m^2$ indicates the patient has a moderate risk of experiencing a major adverse cardiac event within one year from presentation of at least one symptom of ACS and an eGRF level less than or equal to approximately 68 mL/min/1.73 $m^2$ indicates the patient has a high risk of experiencing a major adverse cardiac event within one year from presentation of at least one symptom of ACS. In particular, a patient having a BNP level of less than or equal to approximately 150 pg/mL has an approximately 6.4% incidence of having a major adverse cardiac event within one year from presentation of at least one symptom of ACS. Also, a patient having a BNP level greater than approximately 150 pg/mL has an approximately 27.6% incidence of having a major adverse cardiac event within one year from presentation of at least one symptom of ACS. Further, a patient having a PlGF level less than or equal to approximately 19.5 pg/mL has an approximately 2.4% incidence of having a major adverse cardiac event within one year from presentation of at least one symptom of ACS. Additionally, a patient having a PlGF value of greater than approximately 19.5 pg/mL has an approximately 14.5% incidence of having a major adverse cardiac event within one year from presentation of at least one symptom of ACS. Also, a patient having an eGFR of greater than approximately 68 mL/min/ 1.73 $m^2$ has an approximately 14.3% incidence of having a major adverse cardiac event within one year from presentation of at least one symptom of ACS. Moreover, a patient having an eGFR of less than or equal to approximately 68 mL/min/1.73 $m^2$ has an approximately 36.5% incidence of having a major adverse cardiac event within one year from presentation of at least one symptom of ACS. Also, a patient having a BNP level of less than or equal to approximately 65 pg/mL, has a less than approximately 1% incidence of having a major adverse cardiac event within one year from presentation of at least one symptom of ACS. Further, a patient having a BNP level of greater than approximately 65 pg/mL has an approximately 12.1% incidence of having a major adverse cardiac event within one year from presentation of at least one symptom of ACS.

Additionally, the present invention includes a method of determining incidence of experiencing a major adverse cardiac event, in a patient, within one year from presentation of at least one symptom of ACS comprising the step of: assessing the level of BNP in a test sample from the patient, wherein a BNP level less than or equal to approximately 150 pg/mL indicates that the level of PlGF in said test sample must be assessed and a BNP level greater than approximately 150 pg/mL indicates that the eGRF of said patient must be assessed, wherein if the PlGF level must be assessed, a PlGF level less than or equal to approximately 19.5 pg/mL indicates that the level of HCY in the test sample must be assessed and a PlGF level greater than approximately 19.5 indicates the patient has a moderate risk of experiencing a major adverse cardiac event within one year from presentation of at least one symptom of ACS, wherein if the eGFR must be assessed, an eGFR greater than approximately 68 mL/min/1.73 m$^2$ indicates the patient has a moderate risk of experiencing a major adverse cardiac event within one year from presentation of at least one symptom of ACS and an eGRF level less than or equal to approximately 68 mL/min/1.73 m$^2$ indicates the patient has a high risk of experiencing a major adverse cardiac event within one year from presentation of at least one symptom of ACS, and wherein if said HCY level must be assessed, a HCY level less than or equal to approximately 12.5 μmol/L indicates said patient has a low risk of experiencing a major adverse cardiac event within one year from presentation of at least one symptom of ACS and a HCY level greater than approximately 12.5 μmol/L indicates the patient has a moderate risk of experiencing a major adverse cardiac event within one year from presentation of at least one symptom of ACS. A patient having a BNP level greater than approximately 150 pg/mL has an approximately 27.6% incidence of having a major adverse cardiac event within one year from presentation of at least one symptom of ACS. Further, a patient having a BNP level of less than or equal to approximately 150 pg/mL has an approximately 6.4% incidence of having a major adverse cardiac event within one year from presentation of at least one symptom of ACS. Also, a patient having a PlGF value of greater than approximately 19.5 pg/mL has an approximately 14.5% incidence of having a major adverse cardiac event within one year from presentation of at least one symptom of ACS.

Moreover, a patient having a PlGF level less than or equal to approximately 19.5 pg/mL has an approximately 2.4% incidence of having a major adverse cardiac event within one year from presentation of at least one symptom of ACS. Additionally, a patient having an eGFR of greater than approximately 68 mL/min/1.73 m$^2$, has an approximately 14.3% incidence of having a major adverse cardiac event within one year from presentation of at least one symptom of ACS. Moreover, a patient having an eGFR level of less than or equal to approximately 68 mL/min/1.73 m$^2$ has an approximately 36.5% incidence of having a major adverse cardiac event within one year from presentation of at least one symptom of ACS. Additionally, a patient having a HCY level of less than or equal to 12.5 μmol/L has a less than approximately 1% incidence of having a major adverse cardiac event within one year from presentation of at least one symptom of ACS. Moreover, a patient having a HCY level of greater than approximately 12.5 μmol/L has an approximately 10% incidence of having a major adverse cardiac event within one year from presentation of at least one symptom of ACS.

Also, the present invention encompasses a method of determining risk of experiencing a major adverse cardiac event, in a patient with previously established or diagnosed chronic kidney disease, within one year from presentation of at least one symptom of ACS comprising the steps of: determining whether said patient is cardiac Troponin I negative by comparison with a established reference standard (e.g., cTnI≤approximately 0.015 ng/mL); and assessing the level of BNP in a test sample from said patient, if said patient is cardiac Troponin I negative, wherein a BNP level less than or equal to approximately 150 pg/mL indicates that the level of PlGF in said test sample must be assessed and a BNP level greater than approximately 150 pg/mL indicates that the eGRF of said patient must be assessed, wherein if said PlGF level must be assessed, a PlGF level less than or equal to approximately 19.5 pg/mL indicates that the level of BNP in said test sample must be reassessed, wherein if said level of BNP must be reassessed, a BNP level less than or equal to approximately 65 pg/mL indicates said patient has a low risk of experiencing a major adverse cardiac event within one year from presentation of at least one symptom of ACS and a BNP level greater than approximately 65 pg/mL indicates said patient has a moderate risk of experiencing a major adverse cardiac event within one year from presentation of at least one symptom of ACS, and wherein if eGFR must be assessed, an eGFR level greater than approximately 68 mL/min/1.73 m$^2$ indicates said patient has a moderate risk of experiencing a major adverse cardiac event within one year from presentation of at least one symptom of ACS and an eGRF level less than or equal to approximately 68 mL/min/1.73 m$^2$ indicates said patient has a high risk of experiencing a major adverse cardiac event within one year from presentation of at least one symptom of ACS.

DETAILED DESCRIPTION OF THE INVENTION

Figure 1:
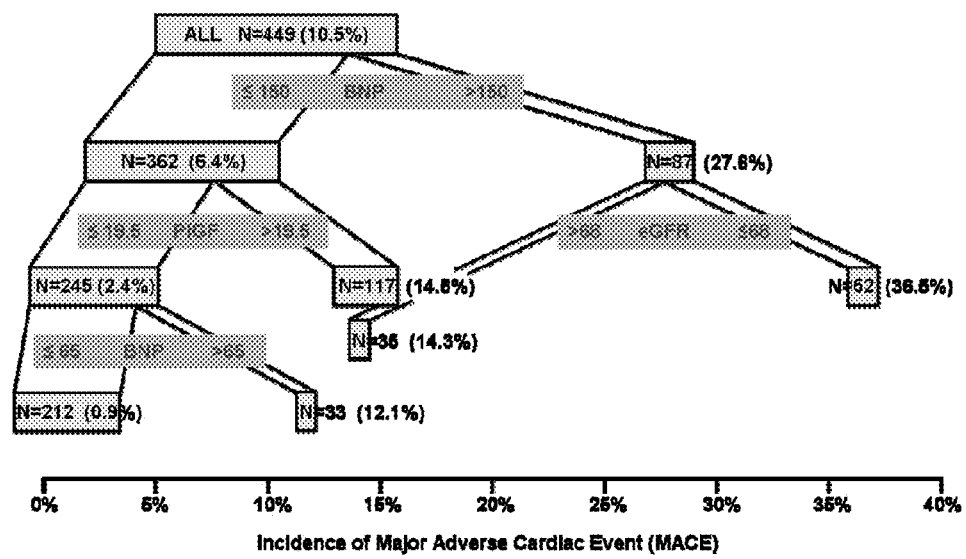
FIG. 1 illustrates how a risk determination is made by utilization of BNP, PlGF and eGFR levels. The number (N) of patients is provided in each category, and the percentage of those patients that had a major adverse cardiac event (MACE) is provided in parentheses. The biomarker and cutoff utilized for each split are indicated. cTnI is included in the analysis but is not as significant as the biomarkers noted above for risk determination.

The present invention relates to the detection and level of combinations of biomarkers (or absence thereof) for the determination of risk (i.e., formulation of a prognosis and risk stratification) associated with the potential occurrence of a major adverse cardiac event (MACE) including, for example, myocardial infarction, death and/or cardiac revascularization. More specifically, the present invention encompasses use of the presence (or absence) and level of at least three biomarkers present in a test sample from a patient. These markers are selected from the group consisting of, for example, cardiac Troponin I (cTnI), B-type natriuretic peptide (BNP), pro-B-type natriuretic peptide (proBNP), NTproBNP (N-terminal pro-B-type natriuretic peptide), placental growth factor (PlGF), homocysteine (HCY), choline, ischemia modified albumin (IMA), soluble CD40 ligand (sCD40L), lipoprotein-associated phospholipase $A_2$ (Lp-$PLA_2$), myeloperoxidase (MPO) and high sensitivity C reactive protein (hsCRP) and may be used, along with estimated glomerular filtration rate (eGFR), in predicting the future occurrence of such a cardiac event, as described above, in an at-risk patient or a patient presenting with clinical symptoms of acute coronary syndrome, or even in an otherwise healthy patient undergoing a complete cardiac assessment. Information as to the presence and level of these biomarkers aids the physician in the determination of a patient's risk of a MACE such that the physician can then prescribe the proper interventional therapy and/or pharmacologic agents for the at-risk patient.

Detection of the presence or absence of such markers, as well as level thereof, may be accomplished by a variety of assay formats well known to those of ordinary skill in the art (see, e.g., The Immunoassay Handbook, $2^{nd}$ Edition, edited by David Wild, Nature Publishing Group, London 2001 incorporated in its entirety by reference). For example, the presence, amount or concentration of the biomarkers described herein (or a fragment thereof) in a test sample can be achieved using an immunoassay such as 1) a sandwich immunoassay (e.g., monoclonal, polyclonal and/or DVD-Ig sandwich immunoassays or any variation thereof (e.g., monoclonal/DVD-Ig or DVD-Ig/polyclonal), including chemiluminescence detection, radioisotope detection (e.g., radioimmunoassay (RIA)) and enzyme detection (e.g., enzyme immunoassay (EIA) or enzyme-linked immunosorbent assay (ELISA) (e.g., Quantikine ELISA assays, R&D Systems, Minneapolis, Minn.))), 2) a competitive inhibition immunoassay (e.g., forward and reverse), 3) a fluorescence polarization immunoassay (FPIA), 4) an enzyme multiplied immunoassay technique (EMIT), 5) a bioluminescence resonance energy transfer (BRET), 6) a homogeneous chemiluminescent assay, 7) a SELDI-based immunoassay, 8) chemiluminescent microparticle immunoassay (CMIA) and 9) a clinical chemistry colorimetric assay (e.g., IMA, creatinine for eGFR determination and LC-MS/MS). (See, e.g., Tietz Textbook of Clinical Chemistry and Molecular Diagnostics. $4^{th}$ Edition, edited by C A Burtis, E R Ashwood and D E Bruns, Elsevier Saunders, St. Louis, Mo., 2006.) The method or methods that may be utilized depend upon the type of biomarker that one wishes to detect, and such methods are well known by those of ordinary skill in the art as noted above.

Further, methods well-known in the art for collecting, handling and processing urine, blood, serum and plasma, and other body fluids, are used in the practice of the present invention. The test sample can comprise further moieties in addition to the analyte of interest, such as antibodies, antigens, haptens, hormones, drugs, enzymes, receptors, proteins, peptides, polypeptides, oligonucleotides and/or polynucleotides. For example, the sample may be a whole blood sample obtained from a subject. It can be necessary or desired that a test sample, particularly whole blood, be treated prior to being subjected to an immunoassay or other assay, as described herein, for example, with a pretreatment reagent. Even in cases where pretreatment is not necessary (e.g., most urine samples), pretreatment optionally can be done (e.g., as part of a regimen on a commercial platform).

Solid supports or phases which may be utilized in the assays described herein are well-known in the art and included, but are not limited to, a magnetic particle, a bead, a test tube, a microtiter plate, a cuvette, a membrane, a scaffolding molecule, a film, a filter paper, a disc and a chip.

Further, if an immunoassay is being utilized, any suitable detectable label as is known in the art can be used. For example, the detectable label can be a radioactive label (such as $^3H$, $^{125}I$, $^{35}S$, $^{14}C$, $^{32}P$, and $^{33}P$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, $2^{nd}$ ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous or heterogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same). Another preferred acridinium compound is an acridinium-9-carboxylate aryl ester. An example of an acridinium-9-carboxylate aryl ester is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Further details regarding acridinium-9-carboxylate aryl ester and its use are set forth in U.S. published application no. 2008-0248493. Chemiluminescent assays (e.g., using acridinium as described above or other chemiluminescent agents) can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. Upon the simultaneous or subsequent addition of at least one basic solution to the sample, a detectable signal, namely, a chemiluminescent signal, indicative of the presence of analyte is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of analyte in the sample can be quantified. Specifically, the amount of analyte in the sample is proportional to the intensity of the signal generated. The amount of analyte present can be quantified by comparing the amount of light generated to a standard curve for the analyte or by comparison to a reference standard. The standard curve can be generated using serial dilutions or solutions of known concentrations of analyte by mass spectroscopy, gravimetric methods, and other techniques known in the art. While the above is described with emphasis on use of an acridinium compound as the chemiluminescent agent, one of ordinary skill in the art can readily adapt this description for use of other chemiluminescent agents.

As noted above, analyte immunoassays generally can be conducted using any format known in the art, such as, but not limited to, a sandwich format. Specifically, in one immunoassay format, at least two antibodies are employed to separate and quantify analyte such as human analyte or a fragment thereof in a sample. More specifically, the at least two antibodies bind to different epitopes on an analyte (or a fragment thereof) forming an immune complex, which is referred to as a "sandwich." Generally, in the immunoassays, one or more antibodies can be used to capture the analyte (or a fragment thereof) in the test sample (i.e., these antibodies are frequently referred to as a "capture" antibody or "capture" antibodies) and one or more antibodies can be used to bind a detectable (namely, quantifiable) label to the sandwich (i.e., these antibodies are frequently referred to as the "detection antibody," the "detection antibodies," the "conjugate," or the "conjugates"). Thus, in the context of a sandwich immunoassay format, an antibody (or a fragment, a variant, or a fragment of a variant thereof) can be used as a capture antibody, a detection antibody, or both. For example, one DVD-Ig having a domain that can bind a first epitope on an analyte (or a fragment thereof) can be used as a capture antibody and/or another DVD-Ig having a domain that can bind a second epitope on an analyte (or a fragment thereof) can be used as a detection antibody. In this regard, a DVD-Ig having a first domain that can bind a first epitope on an analyte (or a fragment thereof) and a second domain that can bind a second epitope on an analyte (or a fragment thereof) can be used as a capture antibody and/or a detection antibody. Alternatively, one DVD-Ig having a first domain that can bind an epitope on a first analyte (or a fragment thereof) and a second domain that can bind an epitope on a second analyte (or a fragment thereof) can be used as a capture antibody and/or a detection antibody to detect, and optionally quantify, two or more analytes.

Generally speaking, in an immunoassay, a sample being tested for (for example, suspected of containing) the biomarker (or a fragment thereof) can be contacted with at least one capture antibody (or antibodies) and at least one detection antibody (which can be a second detection antibody or a third detection antibody or even a successively numbered antibody, e.g., as where the capture and/or detection antibody comprise multiple antibodies) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, described above, a sample suspected of containing the analyte (or a fragment thereof) is first brought into contact with at least one first capture antibody under conditions that allow the formation of a first antibody/analyte complex. If more than one capture antibody is used, a first capture antibody/analyte complex comprising two or more capture antibodies is formed. In a sandwich assay, the antibodies, i.e., preferably, the at least one capture antibody, are used in molar excess amounts of the maximum amount of analyte (or a fragment thereof) expected in the test sample. For example, from about 5 μg to about 1 mg of antibody per mL of buffer (e.g., microparticle coating buffer) can be used.

In contrast, competitive inhibition immunoassays, which are often used to measure small analytes because binding by only one antibody is required, comprise sequential and classic formats. In a sequential competitive inhibition immunoassay, a capture antibody to an analyte of interest is coated onto a well of a microtiter plate or other solid support. When the sample containing the analyte of interest is added to the well, the analyte of interest binds to the capture antibody. After washing, a known amount of labeled analyte (e.g., acridinium, biotin or horseradish peroxidase (HRP)) is added to the well. A substrate for an enzymatic label is necessary to generate a signal. An example of a suitable substrate for HRP is 3,3',5,5'-tetramethylbenzidine (TMB). After washing, the signal generated by the labeled analyte is measured and is inversely proportional to the amount of analyte in the sample. In a classic competitive inhibition immunoassay, an antibody to an analyte of interest is coated onto a solid support (e.g., a well of a microtiter plate). However, unlike the sequential competitive inhibition immunoassay, the sample and the labeled analyte are added to the well at the same time. Any analyte in the sample competes with labeled analyte for binding to the capture antibody. After washing, the signal generated by the labeled analyte is measured and is inversely proportional to the amount of analyte in the sample.

The concentration of analyte (e.g., biomarker) or a fragment thereof in the test sample is determined by appropriate means, such as by use of a standard curve that has been generated using serial dilutions of analyte or a fragment thereof of known concentration. Other than using serial dilutions of analyte or a fragment thereof, the standard curve can be generated gravimetrically, by mass spectroscopy and by other techniques known in the art.

In a chemiluminescent microparticle assay employing the ARCHITECT® analyzer, the conjugate diluent pH may be about 6.0+/−0.2, the microparticle coating buffer may be maintained at about room temperature (i.e., at from about 17 to about 27° C.), the microparticle coating buffer pH may be about 6.5+/−0.2, and the microparticle diluent pH may be about 7.8+/−0.2. Solids preferably are less than about 0.2%, such as less than about 0.15%, less than about 0.14%, less than about 0.13%, less than about 0.12%, or less than about 0.11%, such as about 0.10%. Of course, these ranges or numbers may be altered in order to enhance such properties of the assay including, for example, reduction in background interference, increased sensitivity, increased specificity, etc.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

With regard to the methods of assay (and kit therefor), it may be possible to employ commercially available anti-analyte antibodies or methods for production of anti-analyte as described in the literature. Commercial supplies of various antibodies include, but are not limited to, Santa Cruz Biotechnology Inc. (Santa Cruz, Calif.), GenWay Biotech, Inc. (San Diego, Calif.), and R&D Systems (RDS; Minneapolis, Minn.).

Generally, a predetermined level can be employed as a benchmark against which to assess results obtained upon assaying a test sample for an analyte or a fragment thereof, e.g., for detecting disease or determining risk of disease. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition or with particular clinical indicia can be made. Typically, the predetermined level is obtained with assays of reference subjects (or populations of subjects). The analyte measured can include fragments thereof, degradation products thereof, and/or enzymatic cleavage products thereof.

In particular, with respect to a predetermined level as employed for monitoring disease progression and/or treatment, the amount or concentration of analyte or a fragment thereof may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for analyte is defined in accordance with standard practice. Because the levels of analyte in some instances will be very low, a so-called altered level or alteration can be considered to have occurred when there is any net change as compared to the typical or normal level or range, or reference level or range, which cannot be explained by experimental error or sample variation. Thus, the level measured in a particular sample will be compared with the level or range of levels determined in similar samples from a so-called normal subject. In this context, a "normal subject" is an individual with no detectable disease, for example, and a "normal" (sometimes termed "control") patient or population is/are one(s) that exhibit(s) no detectable disease, respectively, for example. Furthermore, given that analyte is not routinely found at a high level in the majority of the human population, a "normal subject" can be considered an individual with no substantial detectable increased or elevated amount or concentration of analyte, and a "normal" (sometimes termed "control") patient or population is/are one(s) that exhibit(s) no substantial detectable increased or elevated amount or concentration of analyte. An "apparently normal subject" is one in which analyte has not yet been or currently is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, a particular disease, disorder, or condition. The method of assay can also involve the assay of other markers and the like.

Accordingly, the methods described herein also can be used to determine whether or not a subject has or is at risk of developing a given disease, disorder or condition. Specifically, such a method can comprise the steps of: (a) determining the concentration or amount of an analyte (or fragment thereof) in a test sample from a subject using the methods described herein, or methods known in the art; and (b) comparing the concentration or amount of the analyte (or a fragment thereof) determined in step (a) with a predetermined level, wherein, if the concentration or amount of analyte determined in step (a) is favorable with respect to a predetermined level, then the subject is determined not to have or be at risk for a given disease, disorder or condition. However, if the concentration or amount of analyte determined in step (a) is unfavorable with respect to the predetermined level, then the subject is determined to have or be at risk for a given disease, disorder or condition.

Additionally, provided herein is a method of monitoring the progression of disease in a subject. Optimally, the method comprising the steps of: (a) determining the concentration or amount of an analyte (e.g., biomarker) in a test sample from a subject; (b) determining the concentration or amount of the analyte in a later test sample from the subject; and (c) comparing the concentration or amount of analyte as determined in step (b) with the concentration or amount of analyte determined in step (a), wherein if the concentration or amount determined in step (b) is unchanged or is unfavorable when compared to the concentration or amount of analyte determined in step (a), then the disease in the subject is determined to have continued, progressed or worsened. By comparison, if the concentration or amount of analyte as determined in step (b) is favorable when compared to the concentration or amount of analyte as determined in step (a), then the disease in the subject is determined to have discontinued, regressed or improved.

Optionally, the method further comprises comparing the concentration or amount of analyte as determined in step (b), for example, with a predetermined level. Further, optionally the method comprises treating the subject with one or more pharmaceutical compositions for a period of time if the comparison shows that the concentration or amount of analyte as determined in step (b), for example, is unfavorably altered with respect to the predetermined level.

Thus, in particular embodiments, the disclosure also provides a method of determining whether a subject having, or at risk for, a given disease, disorder or condition is a candidate for therapy. Generally, the subject is one who has experienced some symptom of a given disease, disorder or condition or who has actually been diagnosed as having, or being at risk for, a given disease, disorder or condition, and/or who demonstrates an unfavorable concentration or amount of analyte or a fragment thereof, as described herein.

It goes without saying that, while certain embodiments herein are advantageous when employed to assess a given disease, disorder or condition as discussed herein, the assays and kits can be employed to assess analyte in other diseases, disorders and conditions. The method of assay can also involve the assay of other markers and the like.

Kits

A kit for assaying a test sample for the presence, amount or concentration of an analyte (or a fragment thereof) is also encompassed within the scope of the present invention. The kit comprises at least one component for assaying the test sample for the analyte (or a fragment thereof) and instructions for assaying the test sample for the analyte (or a fragment thereof). The at least one component for assaying the test sample for the analyte (or a fragment thereof) can include a composition comprising, for example, an antibody or antibodies against the biomarker or biomarkers (or a fragment, a variant, or a fragment of a variant thereof), which is optionally immobilized on a solid phase.

The kit can comprise at least one component for assaying the test sample for an analyte by assay, e.g., chemiluminescent microparticle immunoassay, and instructions for assaying the test sample for an analyte by immunoassay, e.g., chemiluminescent microparticle immunoassay. For example, the kit can comprise at least one specific binding partner for an analyte such as an anti-analyte, monoclonal/polyclonal antibody (or a fragment thereof that can bind to the analyte, a variant thereof that can bind to the analyte, or a fragment of a variant that can bind to the analyte), either of which can be detectably labeled. Alternatively or additionally, the kit can comprise detectably labeled analyte (or a fragment thereof that can bind to an anti-analyte, monoclonal/polyclonal antibody or an anti-analyte DVD-Ig (or a fragment, a variant, or a fragment of a variant thereof)), which can compete with any analyte in a test sample for binding to an anti-analyte, monoclonal/polyclonal antibody (or a fragment thereof that can bind to the analyte, a variant thereof that can bind to the analyte, or a fragment of a variant that can bind to the analyte) or an anti-analyte DVD-Ig (or a fragment, a variant, or a fragment of a variant thereof), either of which can be immobilized on a solid support. The kit can comprise one or more calibrators or controls, e.g., isolated or purified analyte. The kit can comprise at least one container (e.g., tube, microtiter plates or strips, which can be already coated with a first specific binding partner, for example) for conducting the assay, and/or a buffer, such as an assay buffer or a wash buffer, either one of which can be provided as a concentrated solution, a substrate solution for the detectable label (e.g., an enzymatic label) or a stop solution. Preferably, the kit comprises all components, i.e., reagents, standards, buffers, diluents, etc. which are necessary to perform the assay. The instructions can be in paper form or computer-readable form such as a disk, CD, DVD or the like.

Any antibodies, such as an anti-biomarker antibody or an anti-analyte DVD-Ig, or tracer can incorporate a detectable label as described herein such as a fluorophore, a radioactive moiety, an enzyme, a biotin/avidin label, a chromophore, a chemiluminescent label or the like, or the kit can include reagents for carrying out detectable labeling. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the assay kit reagents, and the standardization of assays.

The kit can also optionally include other reagents required to conduct a diagnostic assay or facilitate quality control evaluations such as buffers, salts, enzymes, enzyme co-factors, enzyme substrates, detection reagents, and the like. Other components, such as buffers and solutions for the isolation and/or treatment of a test sample (e.g., pretreatment reagents) also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. Further, if the detectable label is at least one acridinium compound, the kit also can comprise a source of hydrogen peroxide, such as a buffer, a solution, and/or at least one basic solution. If desired, the kit can contain a solid phase, such as a magnetic particle, bead, test tube, microtiter plate, cuvette, membrane, scaffolding molecule, film, filter paper, disc or chip.

Adaptation of Kits and Methods

The kit (or components thereof), as well as the method of determining the presence, amount or concentration of an analyte in a test sample by an assay, such as the assays described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., an anti-analyte, monoclonal/polyclonal antibody (or a fragment thereof, a variant thereof, or a fragment of a variant thereof) or an anti-analyte DVD-Ig (or a fragment thereof, a variant thereof, or a fragment of a variant thereof) is attached; either way, sandwich formation and analyte reactivity can be impacted), and the length and timing of the capture, detection and/or any optional wash steps. Whereas a non-automated format, such as an ELISA, may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format, such as an ELISA, may incubate a detection antibody, such as the conjugate reagent, for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STATED, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an analyte assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized anti-analyte, monoclonal/polyclonal antibody (or a fragment thereof, a variant thereof, or a fragment of a variant thereof) or anti-analyte DVD-Ig (or a fragment thereof, a variant thereof, or a fragment of a variant thereof), are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge, there is a layer comprising a specific binding partner for an analyte, such as an anti-analyte, monoclonal/polyclonal antibody (or a fragment thereof, a variant thereof, or a fragment of a variant thereof that can bind the analyte) or an anti-analyte DVD-Ig (or a fragment thereof, a variant thereof, or a fragment of a variant thereof that can bind the analyte), either of which can be detectably labeled. Within the fluid pouch of the cartridge is an aqueous reagent that includes p-aminophenol phosphate.

In operation, a sample suspected of containing an analyte is added to the holding chamber of the test cartridge, and the cartridge is inserted into the I-STAT® reader. After the specific binding partner for an analyte has dissolved into the sample, a pump element within the cartridge forces the sample into a conduit containing the chip. Here it is oscillated to promote formation of the sandwich. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte in the sample by means of an embedded algorithm and factory-determined calibration curve.

It further goes without saying that the methods and kits as described herein necessarily encompass other reagents and methods for carrying out the assays. For instance, encompassed are various buffers such as are known in the art and/or which can be readily prepared or optimized to be employed, e.g., for washing, as a conjugate diluent, microparticle diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-Stat cartridge format, using a nucleic acid sequence linked to the signal antibody as a signal amplifier.

OTHER DEFINITIONS

"Biomarker", as used herein, is a characteristic or entity that is objectively measured and evaluated as an indicator of normal biologic processes, pathogenic processes or pharmacologic responses to a therapeutic intervention. This can include physiological indicators such as blood pressure or heart rate and can also refer to compounds or biological entities such as proteins, peptides or small molecules that are produced by the body, released into the bloodstream and are measurable and quantifiable. Included in this definition are also parameters that are based on biomarkers, such as estimated glomerular filtration rate (eGFR) that may be based on creatinine, albumin, blood urea nitrogen, age, gender, ethnic group and body mass.

"ProBNP" or "pro-B-type natriuretic peptide" or "pro-brain natriuretic peptide", as used herein, refers to the 108 amino acid sequence that is derived from the pre-pro BNP molecule. ProBNP is enzymatically processed to form NT-proBNP (amino acids 1-76) and BNP (amino acids 77-108). ProBNP has been shown to circulate in blood (Seferian et al., Clin Chem, 2007; 53:866-873) and may have a role in determining endogenous natriuretic peptide activity in heart failure patients (Lam et al., J Am Coll Cardiol, 2007; 49:1193-1202).

"BNP", as used herein refers to B-type natriuretic peptide which contains 32 amino acids and is 4 kDa. It is involved in the natriuresis system for blood pressure regulation and fluid balance (Bonow, R. O., Circulation 93:1946-1950, 1996). It is the carboxyl terminal (C terminal) 32 amino acids from the precursor proBNP molecule (amino acid numbers 77 to 108). Increased BNP levels are associated with raised atrial and pulmonary wedge pressures as well as reduced ventricular systolic and diastolic function, left ventricular hypertrophy and mycocardial infarction (Sagnella, G. A., Clinical Science 95:519-5219, 1998). BNP is used clinically to aid in the diagnosis of heart failure in patients presenting to the emergency department with dyspnea (i.e., shortness of breath) based on data from the "Breathing Not Properly" trial (Maisel et al., N Engl J. Med. 2003; 347:161-7) and in the risk stratification in ACS patients (Morrow et al., J Am Coll Cardiol. 2003; 41:1264-72).

"N-terminal pro-B-type natriuretic peptide" or "NT-proBNP", as used herein, refers to the inactive amino terminal (N terminal) polypeptide that is cleaved from proBNP. It includes amino acid numbers 1-76 of proBNP. NT-proBNP's clinical utility is very similar to that of BNP with studies supporting its use as an aid in the diagnosis of heart failure in patients presenting with dyspnea (Januzzi et al., Am J Cardiology 2005; 95:948-954).

"Troponin I" or "TnI" (briefly described above) is a 25 kDa inhibitory element of the troponin complex which is found in all striated muscle tissue. The protein binds to actin in the absence of $Ca^{2+}$ thereby inhibiting the ATPase activity of actomyosin. There are several isoforms of the protein. The one found in cardiac tissue (i.e., cTnI) may be present in elevated levels in patients experiencing an acute myocardial infarction or other adverse cardiac events (Khan et al., Am. J. Emerg. Med. 17:225-229, 1999). Free and complexed cardiac troponin I also exist.

"Homocysteine", as used herein, is an amino acid which is also referred to as 2-amino-4-mercaptobutanoic acid. It is a homologue of the amino acid cysteine. A high level of blood serum homocysteine has been determined to be a significant risk factor for cardiovascular disease and stroke (Boushey C J et al., JAMA. 1995; 274:1049-57). However, homocysteine-lowering therapies have failed to reduce cardiovascular event frequency in secondary prevention (Loscalzo, J., N Engl J Med 354(15):1629-1632, 2006). Elevated homocysteine levels have also been associated with increased ischemic injury in patients with ACS (Al-Obaidi M K et al., J Am Coll Cardiol. 2000; 36:1217-22).

"Choline", as used herein, is an organic compound which is a water-soluble essential nutrient and is grouped within the Vitamin B complex. It is a natural, quarternary, saturated amine found in lipids that make up cell membranes and is also found in the neurotransmitter acetylcholine. In particular, choline and its metabolites are required for structural integrity and signaling roles for cell membranes, cholinergic neurotransmission (i.e., acetylcholine synthesis) and as a major source for methyl groups (via its metabolite trimethylglycine) that participate in the S-adenosylmethionine synthesis pathways. It has been hypothesized that choline is released after the stimulation of phospholipase D and the activation of cell surface receptors from various cell types related to plaque destabilization. An increased concentration of choline at hospital admission is a predictor of adverse cardiac events in patients with suspected ACS particularly in troponin negative patients (Danne et al., Am J. Cardiol. 2003; 91:1060-67).

"eGFR" or "estimated glomerular filtration rate" is based on creatinine concentration and calculated based on numerous equations, typically the "Modification in Diet and Renal Disease" equation (MDRD)(Levey et al., Clin Chem, 53(4): 766, 2007) or the Cockcroft-Gault equation.

"Ischemia modified albumin" or "IMA®," as used herein refers to a modification of albumin that occurs in the ischemic state. It is assessed using the albumin cobalt binding test (ACB®) manufactured by Inverness Medical (Waltham, Mass.). This is a clinical chemistry, colorimetric assay that can be performed on numerous clinical chemistry analyzers. The current use of this marker is for "rule-out" of myocardial infarction.

"C-reactive protein", "CRP", "high sensitivity CRP" or "hsCRP", as used herein, is a homopentameric Ca2+-binding acute phase protein which is involved in defense of the host, often in response to inflammation. Studies beginning in the late 1990's identified high normal levels of CRP as indicative of risk of future cardiac disease in healthy men (Ridker, NEJM. 1997; 336:973-979) and were extended to predict future disease in women (Ridker, Circulation. 1998; 98:731-33). CRP assays in the past had low sensitivity and were unable to quantitate values in normal, healthy individuals; therefore, when high sensitivity assays became available, elevated values within the normal range could be measured, and these studies were performed. At the same time, levels of CRP were investigated in more acute cardiac disease for prognosis and risk assessment. Liuzzo et al. (NEJM. 1994: 331:417-24) demonstrated the prognostic utility of CRP in patients with unstable angina.

"PlGF" or "placental growth factor" or "vascular endothelial growth factor-related protein," as used herein, is a protein whose expression, within human atherosclerotic lesions, is associated with plaque inflammation and neovascular growth. (The utility of PlGF in acute cardiac patients was first described by Heeschen et al. (JAMA. 2004; 291:434-441) in patients from the CAPTURE (c7E3 Fab Anti-Platelet Therapy in Unstable Refractory Angina) trial. Upon entry into the trial, baseline samples were collected and evaluated for PlGF and the risk for death or nonfatal myocardial infarction after 30 days was determined. Plasma PlGF level may be an independent biomarker of adverse outcome in patients suspected with ACS, and the single initial measurement appears to extend the predictive and prognostic information gained from traditional inflammatory markers. A further analysis after 4 years (Lenderink er al., J Am Coll Cardiol. 2006; 47:307-11) continued to support the prognostic utility in patients with ACS.)

"Myeloperoxidase" or "MPO" as used herein is a hemoprotein stored in leukocytes and functions in the host-defense mechanisms against a broad range of organisms. Activation of leukocytes results in the secretion of MPO, which catalyzes the hydrogen peroxide mediated peroxidation of halide ions. These products promote the oxidative damage at sites of inflammation. MPO has been linked to inflammation and events involved in early endothelial dysfunction, plaque initiation and progression, development of vulnerable plaque and subsequent complications of atherosclerotic plaque. MPO has been shown to identify troponin negative patients at risk for cardiac events (Baldus et al., Circulation. 2003; 108: 1440-1445) and add more predictive value than other conventional markers (Brennan et al. NEJM. 2003; 349:1595-604).

"LpPLA2" or "lipoprotein-associated phospholipase $A_2$", as used herein, is a vascular-specific inflammatory enzyme implicated in the formation of rupture prone plaque. $LpPLA_2$ cleaves phospholipids into two inflammatory molecules: lysophosphatidylcholine as well as oxidized fatty acids, resulting in a cascade of events leading to atherosclerotic plaque formation. $LpPLA_2$ as measured by the PLAC™ assay (DiaDexus, South San Franciso, Calif.) is used in conjunction with clinical evaluation and patient risk assessment as an aid in predicting risk for coronary heart disease and ischemic stroke associated with atherosclerosis.

"sCD40L" or "soluble CD40 ligand", as used herein, is a member of the tumor necrosis factor (TNF) superfamily and is a multi-functional ligand. CD40L is a 39 kDA glycoprotein that can undergo proteolytic cleave to produce soluble forms of CD40 (15-18 kDa). sCD40L lacks the transmembrane region and a portion of the extracellular domain, but contains the entire TNF-αhomology region.

"Prognosis", as used herein, refers to an increased likelihood that a particular course or outcome will occur. In other words, it is a course or outcome that is more likely to occur in a patient appearing to have a particular disease or condition, when compared to patients not having the disease or condition. One of ordinary skill in the art understands that correlating a prognostic biomarker with the risk of having an adverse event or outcome is based upon a statistical analysis using predefined cutoffs or ranges of the biomarker(s) which serve as reference standards.

"Biological activity" as used herein, refers to all inherent biological properties of the markers described herein (e.g., Troponin I, PlGF and BNP). Such properties include, for example, the ability to bind to the antibodies described herein.

"MACE", as used herein, is defined as a major adverse cardiac event which is an important composite clinic measure of efficacy and safety outcomes for a patient. A MACE includes, for example, cardiac death, heart attack (MI) or ischemia-driven target lesion revascularization.

"Low risk", as used herein, is defined as less than or equal to a ten percent chance, preferably less than a five percent chance and more preferably less than a two percent chance of a patient having a MACE within one year of presentation of at least one symptom of an acute cardiac syndrome (ACS).

"Moderate risk", as used herein, is defined as greater than a ten percent and less than a thirty percent risk of a patient having a MACE within one year of presentation of at least one symptom of an ACS.

"High risk", as used herein, is defined as greater than a twenty-five percent, preferably greater than or equal to a thirty percent and more preferably greater than a thirty-five percent risk of a patient having a MACE within one year of presentation of at least one symptom of an ACS. (It should be noted that the ranges and cutoff points recited herein in connection with the terms "low risk", "moderate risk" and "high risk" may vary depending upon the specific study utilized in order to gather the relevant data in connection with risk assessment. Further, it should be noted that these cutoff points relate to event risk and not relative risk.)

The term "multivalent binding protein" is used in this specification to denote a binding protein comprising two or more antigen binding sites. The multivalent binding protein is preferably engineered to have the three or more antigen binding sites, and is generally not a naturally occurring antibody.

The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference.

"Functional equivalent" as used herein, refers to a protein (e.g., an antibody) having the same characteristics (e.g., binding affinity) of the antibodies to the biomarkers, described herein.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4Immunoglobulin molecules can be of any type (e.g., IgG, IgE, IgM, IgD, IgA and IgY), class (e.g., IgG 1, IgG2, IgG3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., one or more epitopes of the biomarker of interest). It has been shown that the antigen-binding function of an antibody can be performed by one or more fragments of a full-length antibody. Such antibody embodiments may also be bispecific, dual specific, or multi-specific, specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., International Appln. Publication No. WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5). The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Human IgG heavy chain and light chain constant domain amino acid sequences are known in the art.

An "isolated antibody", as used herein, is intended to refer to an antibody that is substantially free of other antibodies having different antigenic specificities (e.g., anisolated antibody that specifically binds at least one epitope of the biomarker of interest and is substantially free of antibodies that specifically bind antigens or epitopes other than those present within the biomarker).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "activity" includes activities such as the binding specificity/affinity of an antibody for an antigen, for example, the antigen or antigens with which antibodies are reactive.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinylated moieties that can be detected by marked avidin (e.g., streptavidin containing a fluorescent marker or enzymatic activity that can be detected by optical or colorimetric methods). As noted above, examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent.

The terms "crystal", and "crystallized" as used herein, refer to an antibody, or antigen-binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ed., pp. 20 1-16, Oxford University Press, New York, N.Y., (1999).

The term "polynucleotide" as referred to herein is a polymeric form of two or more nucleotides, either ribonucleotides or deoxynucleotides or a modified form of either type of nucleotide. The term includes single-stranded and double-stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. Preferably, host cells include prokaryotic and eukaryotic cells selected from any of the Kingdoms of life. Preferred eukaryotic cells include protist, fungal, plant and animal cells. Most preferably, host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The term "regulate" and "modulate" are used interchangeably, and, as used herein, refers to a change or an alteration in the activity of a molecule of interest Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in International Application Publication No. WO 01/83525.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other mammalian or non-mammalian animals. Such substances, as noted above, include, but are not limited to, blood, serum, urine, synovial fluid, cells, organs, tissues (e.g., brain), bone marrow, lymph nodes, cerebrospinal fluid, and spleen.

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

According to the invention and, in particular, for the purpose of assessing the binding affinities of antibodies, a process may be used as described in International Application Publication No. WO 2004/067561, which is incorporated herein by reference. Said process comprises unfolding a natural, recombinant or synthetic peptide or a derivative thereof; exposing the at least partially unfolded peptide or derivative thereof to a detergent, reducing the detergent action and continuing incubation.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following example, which is included for purposes of illustration only and is not intended to limit the scope of the invention.

Example

Prospective Multicenter Clinical Study

A prospective, blinded, multi-center cohort clinical study was performed. The objective of the study was to determine whether biomarker concentrations would provide prognostic value, either independently or in various combinations, to predict (positive predictive value) or rule out (negative predictive value) death, nonfatal MI, or the need for revascularization in patients presenting with ischemic symptoms suggestive of ACS. In addition, the study sought to determine whether the biomarkers could be used to distinguish those patients who presented with chest pain due to cardiac ischemia from noncardiac causes. The study also sought to determine the utility of these biomarkers in the prediction of secondary events including heart failure, need for repeat revascularization, re-hospitalization for ACS or life threatening dysrhythmias.

Patients

Five-hundred-ninety eight (598) patients were enrolled in the study. Eligible patients with ischemic symptoms suggestive of a new NSTEMI/ACS were recruited at presentation to the emergency department. Data regarding clinical characteristics, cardiac procedures and cardiac events during hospitalization were collected. Telephone follow up occurred at 30 days and approximately one year after enrollment to assess for primary and secondary endpoints. MI was adjudicated by a local committee utilizing the joint European Society of Cardiology/American College of Cardiology Committee definition of myocardial infarction (Alpert J S, Thygesen K, et al. Eur Heart J, 2000; 21:1502-13.). Accordingly, either one of the following criteria satisfies the diagnosis for an acute, evolving or recent MI:

1) Typical rise and gradual fall (troponin) or more rapid rise and fall (CK-MB) of biochemical markers of myocardial necrosis with at least one of the following:
   a) ischemic symptoms
   b) development of pathologic Q waves on the ECG
   c) ECG changes indicative of ischemia (ST segment elevation or depression)
   d) coronary artery intervention (e.g., coronary angioplasty)
2) Pathologic findings of an acute MI Inclusion Criteria To be enrolled in the study, a patient must have met the following requirements:
1. Consent form signed prior to the initiation of study-directed activities
2. Women of child bearing years that are not known to be pregnant
3. Age: Minimum of 18 years
4. Presents with at least one sign and/or symptom of ischemia with most recent chest pain within the preceding 12 hours. Signs and/or symptoms of ischemia include:
   Chest pain, pressure, tightness or heaviness, cramping, burning, or aching sensation; chest pain of an accelerating pattern or prolonged [>20 minutes] or recurrent episodes at rest or with minimal effort
   Pain that radiates to neck, jaw, shoulders, back, or 1 or both arms; or unexplained indigestion or "heartburn", belching, epigastric pain, nausea and/or vomiting that may be associated with chest discomfort; and/or associated dyspnea, and/or associated diaphoresis
   Coronary disease, as documented by a history of catheterization, revascularization, or myocardial infarction
   ECG findings consistent with ischemia; examples include
      a new finding of ST-segment depression of at least 0.05 mV, or
      transient (<20 minutes) ST-segment elevation of at least 0.1 mV, or
      T-wave inversion in at least two leads Exclusion Criteria Patients were not enrolled in the study, if the following requirements were met:
1. Persistent (>20 minutes) ST-segment elevation of at least 0.1 mV
2. Unable to understand the objectives of the study
3. Patient is less than 18 years of age
4. Patient is a prisoner Sampling Patient blood samples were obtained at enrollment, 4 to 8 hours later, and if still hospitalized, 12-16 hours after enrollment. Blood was collected and processed to provide five different specimen types (Lithium Heparin Plasma, Lithium Heparin Whole Blood, EDTA Plasma, EDTA Whole Blood, and Serum). Samples were stored centrally at −70° C. prior to analysis.

Biomarker Assays

The cardiac biomarkers were determined without knowledge of the patient's medical history or the treatment ordered. Biomarkers evaluated with the clinical samples as shown in Table 1 include cardiac Troponin-I (cTnI), B-type natriuretic peptide (BNP), N-terminal proBNP (NT-proBNP), C-reactive protein (hsCRP), myeloperoxidase (MPO), placental growth factor (PlGF), choline, lipoprotein-associated phospholipase $A_2$ (LpPLA$_2$), ischemia modified albumin (IMA), soluble CD40 ligand (sCD40L), and Homocysteine (HCY).

These biomarkers were tested to determine whether increased concentrations would predict death, nonfatal MI, or the need for revasularization in this patient population (positive predictive value). The ability of these biomarkers to rule-out future death, nonfatal MI, or the need for revascularization (negative predictive value) was also determined.

Cardiac TnI, BNP, HCY, hsCRP, and creatinine were tested using commercially available ARCHITECT® assays. MPO and PlGF were tested using prototype ARCHITECT assays. Estimated glomerular filtration rate (eGFR) was calculated based on the creatinine value by the MDRD (Modification of Diet and Renal Disease) equation (Levey A S, et al. Clin Chem, 2007; 53:766-72). Choline was measured in Lithium heparin whole blood, Lithium heparin plasma, and EDTA whole blood using an LC-MS/MS method as described (Yue B et al., Clin Chem. 2008:54:590-593). Soluble CD40L was measured by R&D Systems ELISA. IMA was measured with the Albumin Cobalt Binding assay (ACB, Ischemia Technologies Inc.) on a Hitachi instrument. LpPLA$_2$ was measured by ELISA (DiaDexus). NTproBNP was determined on an Ortho Vitros instrument.

TABLE 1

| Biomarker | Method | Study Timepoints Tested (hours) | Sample Type |
|---|---|---|---|
| cardiac Troponin I (cTnI) | ARCHITECT | 0, (4-8), (12-16) | Li Heparin plasma |
| BNP | ARCHITECT | 0, (4-8), (12-16) | EDTA plasma |
| Placental Growth Factor (PlGF) | ARCHITECT | 0, (4-8), (12-16) | EDTA plasma |
| Myeloperoxidase (MPO) | ARCHITECT | 0, (4-8), (12-16) | EDTA & Li Heparin plasma |
| Choline | LC-MS/MS | 0, (4-8), (12-16) | EDTA & Li Heparin Whole Blood Li Heparin plasma |
| C-Reactive Protein (hsCRP) | ARCHITECT | 0, (4-8), (12-16) | Li Heparin plasma |
| Homocysteine (HCY) | ARCHITECT | 0, (4-8), (12-16) | Li Heparin plasma |
| LpPLA$_2$ | DiaDexus | 0, (4-8), (12-16) | Li Heparin plasma |
| NTproBNP | Ortho Vitros | 0 | Serum |
| sCD40 ligand | R&D Systems | 0, (4-8), (12-16) | Li Heparin plasma |
| Ischemia Modified Albumin (IMA) | Inverness | 0 | Serum |
| Creatinine | ARCHITECT | 0 | Serum |

Summary of Results and Major Adverse Cardiac Events

A total of 598 patients were enrolled in the study; however, 55 patients did not have follow up information available. To further focus on the prognostic utility of the biomarkers, another 40 patients that suffered from a major adverse cardiac event in the initial 24 hrs after presentation were removed from the analysis set. To evaluate the utility of each biomarker in all the patients, another 53 patients were removed due to missing biomarker values from the laboratory. This left a total of 449 patients to be evaluated. Table 2 shows the baseline characteristics for this patient population. There were 47 (10.5% incidence) combined major adverse cardiac events in this patient group. The major adverse cardiac events consist of 19 deaths (4.2% incidence), 7 myocardial infarctions (1.6% incidence), and 21 revascularizations (4.7% incidence).

TABLE 2

|  | Total (n = 449) | Patients Without MACE (n = 402) | Patients With MACE (n = 47) | p-value[b] |
|---|---|---|---|---|
| Characteristic | | | | |
| Age - Mean (SD) | 54 (13.8) | 53 (13.4) | 65 (12.6) | <0.0001 |
| Age ≥65 - no. (%) | 107 (23.8) | 81 (20.1) | 26 (55.3) | 0.2066 |
| Female Gender - no. (%) | 209 (46.5) | 194 (48.3) | 15 (31.9) | 0.0335 |
| Diabetes Mellitus - no. (%) | 103 (22.9) | 81 (20.1) | 22 (46.8) | <0.0001 |
| Hypertension - no. (%) | 270 (60.5) | 235 (58.9) | 35 (74.5) | 0.0389 |
| Current Tobacco User - no. (%) | 146 (32.9) | 132 (33.2) | 14 (29.8) | 0.6328 |
| Lung Disease - no. (%) | 33 (7.4) | 24 (6.0) | 9 (19.1) | 0.0011 |
| Dyslipidemia - no. (%) | 172 (39.2) | 146 (37.2) | 26 (56.5) | 0.0109 |
| Body Mass Index - Mean (SD)[a] | 31.8 (15.44) | 32.3 (16.30) | 28.9 (6.78) | 0.0252 |
| eGFR - Mean (SD) | 87.4 (32.05) | 89.5 (31.75) | 69.7 (29.33) | <0.0001 |
| Cardiovascular History - no. (%) | | | | |
| History of Coronary Artery Disease | 131 (29.2) | 102 (25.4) | 29 (63.0) | <0.0001 |
| Prior Myocardial Infarction | 80 (17.8) | 64 (15.9) | 16 (34.0) | 0.0021 |
| Prior Congestive Heart Failure | 63 (14.2) | 47 (11.8) | 16 (34.0) | <0.0001 |
| TIMI Risk Score - no. (%)[a] | | | | <0.0001 |
| 0-2 | 281 (70.4) | 264 (73.9) | 17 (40.5) | |
| 3-4 | 111 (27.8) | 88 (24.6) | 23 (54.8) | |
| 5-7 | 7 (1.8) | 5 (1.4) | 2 (4.8) | |
| Medication Use at ED Presentation | | | | |
| Aspirin - no. (%) | 179 (40.0) | 154 (38.5) | 25 (53.2) | 0.0518 |
| Statin - no. (%) | 142 (31.8) | 116 (29.0) | 26 (55.3) | 0.0002 |
| ACE Inhibitor - no. (%) | 125 (28.0) | 103 (25.8) | 22 (46.8) | 0.0024 |

[a]Variable missing greater than 10% of responses
[b]Wilcoxon Score Test was used for continuous variables and Chi-square Test was used for categorical variables
MACE = Major adverse cardiac event;
TIMI = thrombolysis in myocardial infarction;
ED = emergency department,
eGFR = estimated glomerular filtration rate a) Discrimination Power of Laboratory Parameters, Gender, and Age The maximum biomarker value from all available time-points was used for the subsequent analysis. Each biomarker and laboratory parameter were independently categorized into several dichotomous variables (as defined by 10% intervals) to identify the dichotomy that reveals the strongest association with the incidence of major adverse cardiac event at one year. The chi-square test was used to determine the optimal cutoff. The relative risk for each biomarker at the optimal cutoff was then determined The dichotomies for each biomarker with the optimal cutoff, chi-square value, and relative risk is shown in Table 3

TABLE 3

| Biomarker | Cutoff | Incidence % (n) if > cutoff | Incidence % (n) if ≤ cutoff | p-value | Chi$^2$ Value | Relative Risk (95% Confidence Interval) |
|---|---|---|---|---|---|---|
| NTproBNP† | 1200 pg/mL | 40.0% (50) | 6.6% (348) | <0.0001 | 50.6 | 6.1 (3.6-10.2) |
| BNP | 150 pg/mL | 27.6% (87) | 6.4% (362) | <0.00001 | 33.7 | 4.3 (2.6-7.3) |
| Age | 65 years | 26.0% (96) | 6.2% (353) | <0.00001 | 31.6 | 4.2 (2.5-7.1) |
| cTnI | 0.015 ng/mL | 26.4% (87) | 6.6% (362) | <0.00001 | 29.4 | 4.0 (2.4-6.7) |
| HCY | 12.5 μmol/L | 22.8% (114) | 6.3% (335) | <0.00001 | 24.8 | 3.6 (2.1-6.2) |
| eGFR* | 68 mL/min/1.73 m$^2$ | 6.3% (319) | 20.8% (130) | <0.0001 | 20.7 | 3.3 (1.9-5.7) |
| PlGF | 20 pg/mL | 18.4% (158) | 6.2% (291) | <0.001 | 16.2 | 3.0 (1.7-5.2) |
| Choline (plasma) | 15.3 μmol/L | 20.5% (112) | 7.1% (337) | <0.001 | 16.1 | 2.9 (1.7-4.9) |
| hsCRP | 13 mg/L | 20.0% (90) | 8.1% (359) | <0.01 | 10.9 | 2.5 (1.4-4.3) |
| IMA | 144 U/mL | 27.3% (22) | 9.6% (427) | <0.05 | 7.0 | 2.8 (1.4-6.0) |
| LpPLA2 | 240 ng/mL | 13.9% (230) | 6.8% (219) | <0.05 | 6 | 2.0 (1.1-3.6) |
| Gender | male | 13.3% (240) | 7.2% (209) | <0.05 | 4.5 | 1.9 (1.0-3.3) |
| Choline (lithium heparin whole blood) | 49 μmol/L | 15.7% (89) | 9.2% (360) | 0.08 | 3.3 | 1.7 (1.0-3.1) |
| MPO (lithium heparin plasma) | 2000 pmol/L | 15.5% (71) | 9.5% (378) | 0.14 | 2.3 | 1.6 (0.9-3.0) |
| MPO (EDTA | 200 pmol/L | 12.0% (291) | 7.6% (158) | 0.15 | 2.1 | 1.6 (0.8-3.0) |

TABLE 3-continued

| Biomarker | Cutoff | Incidence % (n) if > cutoff | Incidence % (n) if ≤ cutoff | p-value | Chi$^2$ Value | Relative Risk (95% Confidence Interval) |
|---|---|---|---|---|---|---|
| plasma) | | | | | | |
| Choline (EDTA whole blood) | 40 μmol/L | 13.6% (88) | 9.7% (361) | 0.33 | 1.2 | 1.4 (0.8-2.6) |
| Soluble CD40L | 760 pg/mL | 7.0% (114) | 11.6% (335) | 0.21 | 1.9 | 0.6 (0.3-1.3) |

†missing greater than 10% of data points
*eGFR effect is reversed: Patients with values less than the cutoff have a worse prognosis.

Several biomarkers including NTproBNP, BNP, cTnI, HCY, PlGF, plasma Choline, IMA, hsCRP, displayed significant predictive values for major adverse cardiac events. Age and estimated glomerular filtration rate (eGFR) were also significant. The highest relative risks were observed for NTproBNP (6.1), BNP (4.3), age (4.2) and cTnI (4.0).

Collinearity between BNP and cTnI was observed using a BNP cutoff of less than or equal to 150 pg/mL and a cTnI cutoff of less than or equal to 0.015 ng/mL. 375 patients have identical results where 325 are below the cutoffs in both assays and 50 are above the cutoffs in both assays. Both assays identify 18 major adverse cardiac events, and they both miss 18 major adverse cardiac events. BNP identifies 6 major adverse cardiac events that are missed by cTnI whereas cTnI identifies 5 major adverse cardiac events that are missed by BNP.

b) CART Analysis

CART (Classification and Regression Tree) analysis (see Muller R. Clin Chim Acta. 2008; 394:1-6.) was utilized for multimarker analysis. BNP has the highest chi-square value and therefore the most significant association with prognosis or risk stratification of patients. As shown in FIG. 1, a BNP cutoff of 150 pg/mL was used in the first split. There are 362 patients that have a BNP value less than or equal to 150 pg/mL with a 6.4% incidence of having a major adverse cardiac event and 87 patients that have a BNP value greater than 150 pg/mL with a 27.6% incidence of having a major adverse cardiac event. Estimated GFR (eGFR) was then used to further differentiate the 87 patients with a BNP value greater than 150 pg/mL. Using an eGFR cutoff of 68 mL/min/1.73 m$^2$, 52 patients are in a high risk category with a 36.5% incidence of having a major adverse cardiac event and 35 patients have eGFR greater than 68 mL/min/1.73 m$^2$ with a 14.3% incidence of having a major adverse cardiac event.

PlGF was used to differentiate the 362 patients with BNP value less than or equal to 150 pg/mL (see FIG. 1). Using a PlGF cutoff of 19.5 pg/mL, there are 245 patients with PlGF less than or equal to 19.5 pg/mL that have a 2.4% incidence of having a major adverse cardiac event and 117 patients with PlGF greater than 19.5 pg/mL that have a 14.5% incidence of having a major adverse cardiac event. The 245 patients with PlGF less than or equal to 19.5 pg/mL can be further split based on a BNP value of 65 pg/mL. There are 212 patients with BNP less than or equal to 65 pg/mL in the low risk category with a 0.9% incidence (99.1% negative predictive value) of having a major adverse cardiac event and 33 patients with BNP greater than 65 pg/mL with a 12.1% incidence of having a major adverse cardiac event.

The combination of BNP, PlGF, and eGFR is able to stratify the patient population into low, moderate, and high risk groups. The low risk group contains 212 patients with a less than 1% incidence of having a major adverse cardiac event while the high risk group contains 52 patients with a 36.5% incidence of having a major adverse cardiac event. There are 185 patients in the moderate risk group with a 12.1% to 14.5% incidence of having a major adverse cardiac event (see FIG. 1).

A sensitivity analysis was done to evaluate BNP and NTproBNP at different cutoffs. Both BNP and NTproBNP provide a statistically significant relative risk across a wide range of cutoff values. BNP was evaluated from 40 to 180 pg/mL, as shown in Table 4, and NTproBNP was evaluated from 125 to 1,200 pg/mL as shown in Table 5.

TABLE 4

| BNP cutoff (pg/mL) | Incidence if > cutoff (n) | Incidence if ≤ cutoff (n) | p-value | Relative Risk (95% Confidence interval) |
|---|---|---|---|---|
| 180 | 27.4% (73) | 7.2% (376) | <0.0001 | 3.8 (2.3-6.4) |
| 150 | 27.6% (87) | 6.4% (362) | <0.0001 | 4.3 (2.6-7.3) |
| 120 | 27.7% (101) | 5.5% (348) | <0.0001 | 5.1 (3.0-8.7) |
| 80 | 23.2% (138) | 4.8% (311) | <0.0001 | 4.8 (2.7-8.6) |
| 60 | 21.7% (161) | 4.2% (288) | <0.0001 | 5.2 (2.8-9.8) |
| 40 | 19.4% (206) | 2.9% (243) | <0.0001 | 6.7 (3.1-14.7) |

TABLE 5

| NTproBNP cutoff (pg/mL) | Incidence if > cutoff (n) | Incidence if ≤ cutoff (n) | p-value | Relative Risk (95% Confidence interval) |
|---|---|---|---|---|
| 1,200 | 40.0% (50) | 6.6% (348) | <0.0001 | 6.1 (3.6-10.2) |
| 900 | 36.1% (61) | 6.2% (337) | <0.0001 | 5.8 (3.4-9.9) |
| 450 | 27.2% (92) | 5.9% (306) | <0.0001 | 4.6 (2.6-8.1) |
| 125 | 19.8% (187) | 2.8% (211) | <0.0001 | 7.0 (3.0-16.1) |

In the subset of patients with a BNP value less than or equal to 150 pg/mL or less than or equal to 60 pg/mL, the relative risk using PlGF remained statistically significant when the cutoff was evaluated from 18 to 22 pg/mL (Table 6).

TABLE 6

|  | PlGF cutoff (pg/mL) | Incidence if > cutoff (n) | Incidence if ≤ cutoff (n) | p-value | Relative Risk (95% Confidence interval) |
|---|---|---|---|---|---|
| BNP ≤150 pg/mL | 22 | 16.3% (80) | 3.5% (282) | 0.0001 | 4.6 (2.1-10.1) |
|  | 19.5 | 14.5% (117) | 2.4% (245) | 0.0001 | 5.9 (2.4-14.7) |
|  | 18 | 11.2% (161) | 2.5% (201) | 0.0024 | 4.5 (1.7-11.8) |
| BNP ≤60 pg/mL | 22 | 14.0% (50) | 2.1% (238) | 0.0008 | 6.7 (2.2-20.2) |
|  | 19.5 | 12.7% (79) | 1.0% (209) | 0.0007 | 13.2 (3.0-59.1) |
|  | 18 | 8.5% (117) | 1.2% (171) | 0.0093 | 7.3 (1.6-32.8) |

Figure 2:
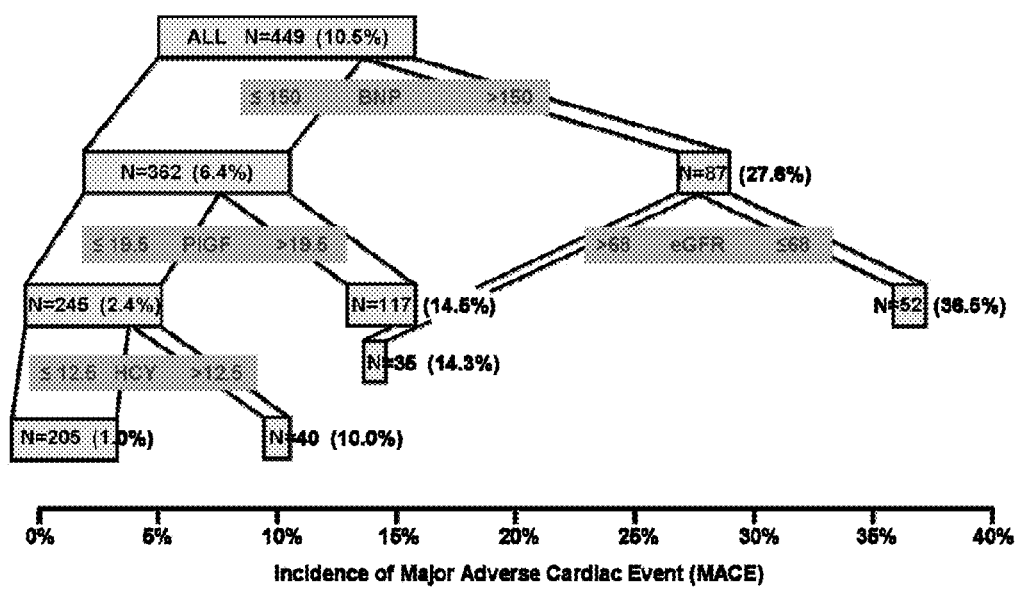
FIG. 2 illustrates how a risk determination is made based upon use of levels of BNP, PlGF, HCY and eGFR. The number (N) of patients is provided in each category and the percentage of those patients that had a major adverse cardiac event (MACE) is provided in parentheses. The biomarker and cutoff utilized for each split is indicated. Again, cTnI is included in the analysis but is not as significant as the biomarkers described above for risk determination.

Similar to the analysis described in FIG. 1, HCY can be substituted for BNP to further differentiate the patients with PlGF less than or equal to 19.5 pg/mL. As shown in FIG. 2, there are 205 patients with HCY less than or equal to 12.5 μmol/L that have a 1.0% incidence of a major adverse cardiac event and 40 patients with HCY greater than 12.5 μmol/L that have a 10.0% incidence of having a major adverse cardiac event.

As shown in FIG. 2, the combination of BNP, PlGF, HCY, and eGFR is also able to stratify the patient population into low, moderate, and high risk groups. The low risk group contains 205 patients with a 1% incidence (99% negative predictive value) of having a major adverse cardiac event while the high risk group contains 52 patients with a 36.5% incidence of having a major adverse cardiac event. There are 192 patients in the moderate risk group that have a 10.0% to 14.5% incidence of having a major adverse cardiac event.

Figure 3:
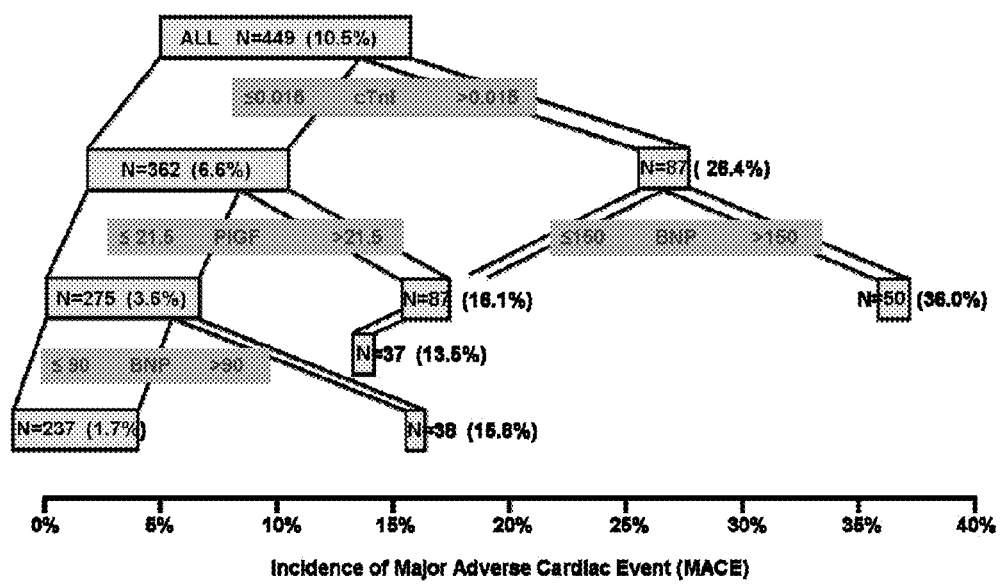
FIG. 3 illustrates how a risk determination is made based upon use of levels of cTnI, BNP and PlGF. The number (N) of patients is provided in each category and the percentage of those patients that had a major adverse cardiac event (MACE) is provided in parentheses. The biomarker and cutoff utilized for each split are indicated.
Figure 4:
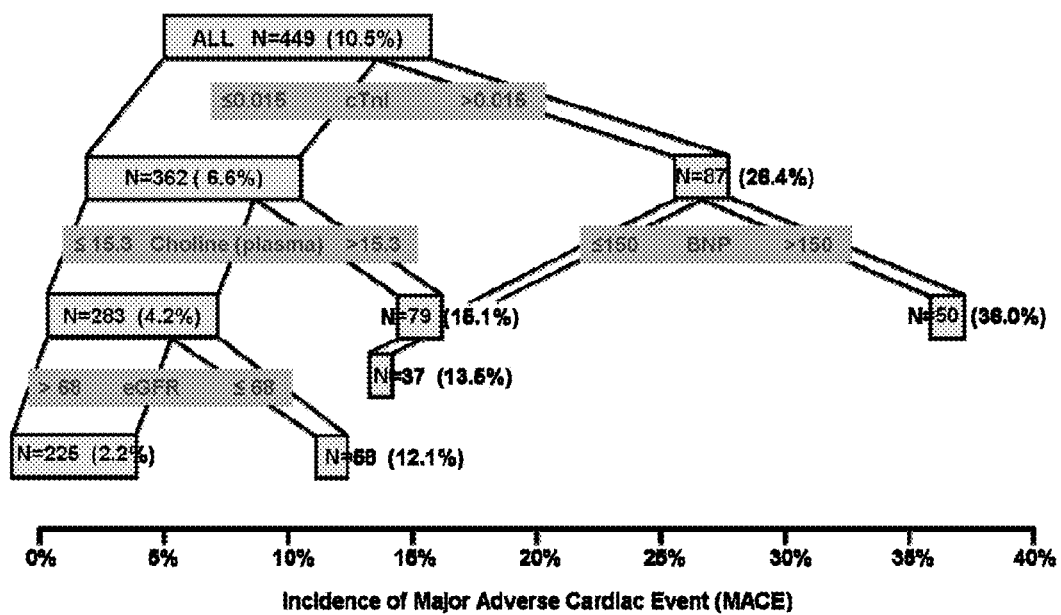
FIG. 4 illustrates how a risk determination is made based upon use of levels of cTnI, BNP, Choline (plasma), and eGFR. The number (N) of patients is provided in each category and the percentage of those patients that had a major adverse cardiac event (MACE) is provided in parentheses. The biomarker and cutoff utilized for each split are indicated.

Due to the collinearity observed between BNP and cTnI, additional CART analyses were performed in which cTnI was used in the first split in place of BNP as shown in FIGS. 3 and 4. In FIG. 3, a cTnI cutoff of less than or equal to 0.015 ng/mL was used in the first split. There are 362 patients that have cTnI less than or equal to 0.015 ng/mL with a 6.6% incidence of having a major adverse cardiac event and 87 patients with cTnI greater than 0.015 ng/mL that have a 26.4% incidence of having a major adverse cardiac event. BNP was then used to further differentiate the 87 patients with a cTnI value greater than 0.015 ng/mL. There are 50 patients with BNP greater than 150 pg/mL with a 36.0% incidence of having a major adverse cardiac event and 37 patients with BNP less than or equal to 150 pg/mL with a 13.5% incidence of having a major adverse cardiac event.

PlGF was used to differentiate the 362 patients with a cTnI value less than or equal to 0.015 ng/mL (see FIG. 3). In this case, a PlGF cutoff of 21.5 pg/mL was used; there are 275 patients with PlGF less than or equal to 21.5 pg/mL that have a 3.6% incidence of having a major adverse cardiac event and 87 patients with PlGF greater than 21.5 pg/mL that have a 16.1% incidence of having a major adverse cardiac event. The 275 patients can be further split based on a BNP value of 90 pg/mL. There were 237 patients with BNP less than or equal to 90 pg/mL with a 1.7% incidence of having a major adverse cardiac event and 38 patients with BNP greater than 90 pg/mL with a 15.8% incidence of having a major adverse cardiac event.

As shown in FIG. 3, the combination of cTnI, BNP, and PlGF is also able to stratify the patient population into low, moderate, and high risk groups. The low risk group contains 237 patients with less than 2% incidence of having a major adverse cardiac event, while the high risk group contains 50 patients with a 36% incidence of having a major adverse cardiac event. There are 162 patients in the moderate risk group with a 13.5% to 16.1% incidence of having a major adverse cardiac event.

An alternative analysis to that described in FIG. 3 is shown in FIG. 4 where the plasma choline result was substituted for PlGF. In this case, a cutoff of 15.3 μmol/L was used for choline, and there are 283 patients with choline less than or equal to 15.3 μmol/L that have a 4.2% incidence of having a major adverse cardiac event. There are 79 patients with choline greater than 15.3 μmol/L that have a 15.1% incidence of having a major adverse cardiac event. An eGFR cutoff of 68 mL/min/1.73 m$^2$ was then used to differentiate the 283 patients with choline less than or equal to 15.3 μmol/L. There are 225 patients with eGFR greater than 68 mL/min/1.73 m$^2$ that have a 2.2% incidence of having a major adverse cardiac event and 58 patients with eGFR less than or equal to 68 mL/min/1.73 m$^2$ that have a 12.1% incidence of having a major adverse cardiac event.

As shown in FIG. 4, the combination of cTnI, plasma choline, BNP, and eGFR is also able to stratify the patient population into low, moderate, and high risk groups. The low risk group contains 225 patients with a 2.2% incidence of having a major adverse cardiac event while the high risk group contains 50 patients with a 36% incidence of having a major adverse cardiac event. There are 174 patients in the moderate risk group with a 12.1% to 15.1% incidence of having a major adverse cardiac event.

The biomarkers that are statistically significant in this study are: NTproBNP, BNP, cTnI, HCY, eGFR, PlGF, Choline, IMA, and hsCRP. The biomarkers (listed in Table 3) fall within different pathophysiologic pathways (Vasan R S, Circulation, 2006; 113:2335-2362 and Apple F S, Clin Chem. 2005; 51:810-824). Based on the different pathophysiology of biomarkers, a combination or combinations of biomarkers would be beneficial to assist in the risk stratification of patients. Biomarker combinations would include at least three biomarkers from the markers discussed above.

What is claimed is:

1. A method of determining risk of experiencing a major adverse cardiac event (MACE), in a patient, within one year from presentation of at least one symptom of acute coronary syndrome (ACS) comprising the steps of:
    a) obtaining a test sample from said patient;
    b) determining the amount of at least three biomarkers selected from the group consisting of cardiac Troponin I (cTnI), pro-B-type natriuretic peptide (proBNP) or a cleavage product thereof, high sensitivity C reactive protein (hsCRP), myeloperoxidase (MPO), placental growth factor (PlGF), estimated glomerular filtration rate (eGFR), homocysteine (HCY), choline, ischemia modified albumin (IMA), soluble CD40 ligand (sCD40L) and lipoprotein-associated phospholipase $A_2$ (LpPLA2) in said test sample; and
    c) comparing the amount of said at least three biomarkers to biomarker reference standards, wherein said risk is determined by results of said comparison.

2. The method of claim 1, wherein said at least three biomarkers are selected from the group consisting of proBNP or a cleavage product thereof, PlGF, eGRF and homocysteine.

3. The method of claim 1, wherein said at least three biomarkers are selected from the group consisting of proBNP or a cleavage product thereof, PlGF and eGFR.

4. The method of claim 1, wherein said at least three biomarkers are selected from the group consisting of cTnI, proBNP or a cleavage product thereof and PlGF.

5. The method of claim 1, wherein said at least three biomarkers are selected from the group consisting of cTnI, proBNP or a cleavage product thereof, choline and eGFR.

6. The method of claim 1, wherein said test sample is selected from the group consisting of blood, serum, and plasma.

7. The method of claim 1, wherein said cleavage product is BNP or NT-proBNP.

8. The method of claim 1, wherein said results are used to determine risk of experiencing a major adverse cardiac event within one year of presentation of at least one symptom of acute coronary syndrome subsequent to stress testing undergone by said patient.

9. The method of claim 1, wherein said major adverse cardiac event comprises at least one condition selected from the group consisting of a myocardial infarction, death, revascularization, repeat revascularization, stroke, heart failure and dysrhymias.

* * * * *